(12) United States Patent
Mazumder et al.

(10) Patent No.: US 10,470,475 B2
(45) Date of Patent: *Nov. 12, 2019

(54) DATA OUTPUT FOR HIGH FREQUENCY DOMAIN

(71) Applicant: MICRON TECHNOLOGY, INC., Boise, ID (US)

(72) Inventors: Kallol Mazumder, Plano, TX (US); Myung-Ho Bae, McKinney, TX (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/197,871

(22) Filed: Nov. 21, 2018

(65) Prior Publication Data
US 2019/0090499 A1    Mar. 28, 2019

Related U.S. Application Data

(63) Continuation of application No. 15/652,986, filed on Jul. 18, 2017, now Pat. No. 10,157,648.

(51) Int. Cl.
*G11C 7/10* (2006.01)
*A23C 3/07* (2006.01)
(Continued)

(52) U.S. Cl.
CPC .............. *A23C 3/076* (2013.01); *A23C 9/206* (2013.01); *A23L 2/50* (2013.01); *A23L 3/28* (2013.01); *C02F 1/003* (2013.01); *C02F 1/008* (2013.01); *C02F 1/325* (2013.01); *C02F 1/725* (2013.01); *G01N 21/33* (2013.01); *G01N 21/53* (2013.01); *G01N 21/6486* (2013.01); *G01N 21/94* (2013.01); *G01N 33/18* (2013.01); *A23V 2002/00* (2013.01); *C02F 1/283* (2013.01); *C02F 1/44* (2013.01); *C02F 2201/009* (2013.01); *C02F 2201/326* (2013.01); *C02F 2201/3222* (2013.01); *C02F 2201/3227* (2013.01); *C02F 2209/001* (2013.01);
(Continued)

(58) Field of Classification Search
CPC ................................ G11C 7/106; G11C 7/222
See application file for complete search history.

(56) References Cited

U.S. PATENT DOCUMENTS 6,249,483 B1    6/2001 Kim
7,447,110 B2    11/2008 Chae
(Continued)

OTHER PUBLICATIONS

PCT International Search Report & Written Opinion for PCT Application No. PCT/US2018/028409 dated Aug. 31, 2018; 12 Pages.

*Primary Examiner* — Hien N Nguyen
(74) *Attorney, Agent, or Firm* — Fletcher Yoder, PC.

(57) ABSTRACT

A system includes memory banks that store data and a data path coupled to the memory banks that transfers the data. The system also includes a latch that gates the data path based on a clock signal in the system. The system further includes interface circuitry coupled to the data path that sends an instruction to the memory banks to transmit the data on the data path in response to receiving a first rising edge of the clock signal. The interface circuitry also outputs gated data in response to receiving a second rising edge of the clock signal. The latch gates the data path to store the gated data in response to receiving a falling edge of the clock signal.

22 Claims, 11 Drawing Sheets

(51) Int. Cl.
    *C02F 1/32*     (2006.01)
    *A23L 2/50*     (2006.01)
    *A23L 3/28*     (2006.01)
    *C02F 1/72*     (2006.01)
    *A23C 9/20*     (2006.01)
    *G01N 21/94*     (2006.01)
    *G01N 21/64*     (2006.01)
    *G01N 21/53*     (2006.01)
    *G01N 21/33*     (2006.01)
    *C02F 1/00*     (2006.01)
    *G01N 33/18*     (2006.01)
    *C02F 1/28*     (2006.01)
    *C02F 1/44*     (2006.01)

(52) U.S. Cl.
CPC .. *C02F 2209/003* (2013.01); *C02F 2209/006* (2013.01); *C02F 2209/008* (2013.01); *C02F 2209/02* (2013.01); *C02F 2209/08* (2013.01); *C02F 2209/11* (2013.01); *C02F 2209/15* (2013.01); *C02F 2209/20* (2013.01); *C02F 2209/21* (2013.01); *C02F 2303/04* (2013.01); *C02F 2305/10* (2013.01); *C02F 2307/02* (2013.01); *C02F 2307/04* (2013.01); *C02F 2307/10* (2013.01); *G01N 2201/062* (2013.01); *Y02A 20/212* (2018.01); *Y02W 10/37* (2015.05)

(56) References Cited

U.S. PATENT DOCUMENTS

| | | |
|---|---|---|
| 9,460,803 B1 | 10/2016 | Tang et al. |
| 10,157,648 B1 * | 12/2018 | Mazumder ........... G11C 7/1066 |
| 2004/0196732 A1 | 10/2004 | Lee |
| 2006/0090108 A1 | 4/2006 | Seyyedy et al. |
| 2010/0287401 A1 | 11/2010 | Espinoza et al. |

* cited by examiner

DATA OUTPUT FOR HIGH FREQUENCY DOMAIN

CROSS REFERENCE TO RELATED APPLICATIONS

This application is a continuation of U.S. patent application Ser. No. 15/652,986, entitled "DATA OUTPUT FOR HIGH FREQUENCY DOMAIN," filed Jul. 18, 2017, which is hereby incorporated by reference in its entirety for all purposes.

BACKGROUND

Field of the Present Disclosure

Embodiments of the present disclosure relate generally to the field of semiconductor devices. More specifically, embodiments of the present disclosure relate to data output by a semiconductor device operating in a high frequency domain.

Description of Related Art

A semiconductor device, such as a microcomputer, memory, gate array, among others, may output requested data in response to an instruction (e.g., from a controller communicatively coupled to the semiconductor device) requesting the requested data. For example, in response to receiving a falling edge of a clock signal in the semiconductor device, an instruction may be sent to transmit the requested data on a data path of the semiconductor device after an output delay (e.g., associated with outputting the data on the data path). In response to receiving an immediately subsequent rising edge of the clock signal, the requested data may be output from the semiconductor device (e.g., via an input/output interface) by outputting the data path (e.g., while the clock signal is high). As such, the time between sending the instruction to transmit the requested data on the data path and outputting the data path is one-half a period of the clock signal.

However, in some high frequency domains, at least some of the data output from the data path may not be the requested data, resulting in no data or the wrong data being output from the semiconductor device. In such high frequency domains, the output delay associated with sending the requested data on the data path may be greater than the time between sending the instruction to transmit the requested data on the data path and outputting the data path (i.e., one-half a period of the clock signal). As such, at least some of the data output from the data path may not be the requested data.

Embodiments of the present disclosure may be directed to one or more of the problems set forth above.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, in response to receiving a first rising edge of a clock signal in a semiconductor device, an instruction may be sent to transmit data on a data path of the semiconductor device. In response to receiving a first falling edge of the clock signal, the data path may be gated to store gated data. In response to receiving a second rising edge of the clock signal, the gated data may then be output (e.g., by the semiconductor device). As such, the time between sending the instruction to transmit the requested data on the data path and outputting the gated data is a period of the clock signal. The period of the clock signal may be greater or equal to an output delay associated with sending the requested data on the data path, thus preventing no data or wrong data from being read in high frequency domains. Moreover, gating the data path may ensure that the requested data is outputted for lower frequency domains. In this manner, the requested data may be correctly output from the semiconductor device.

Figure 1:
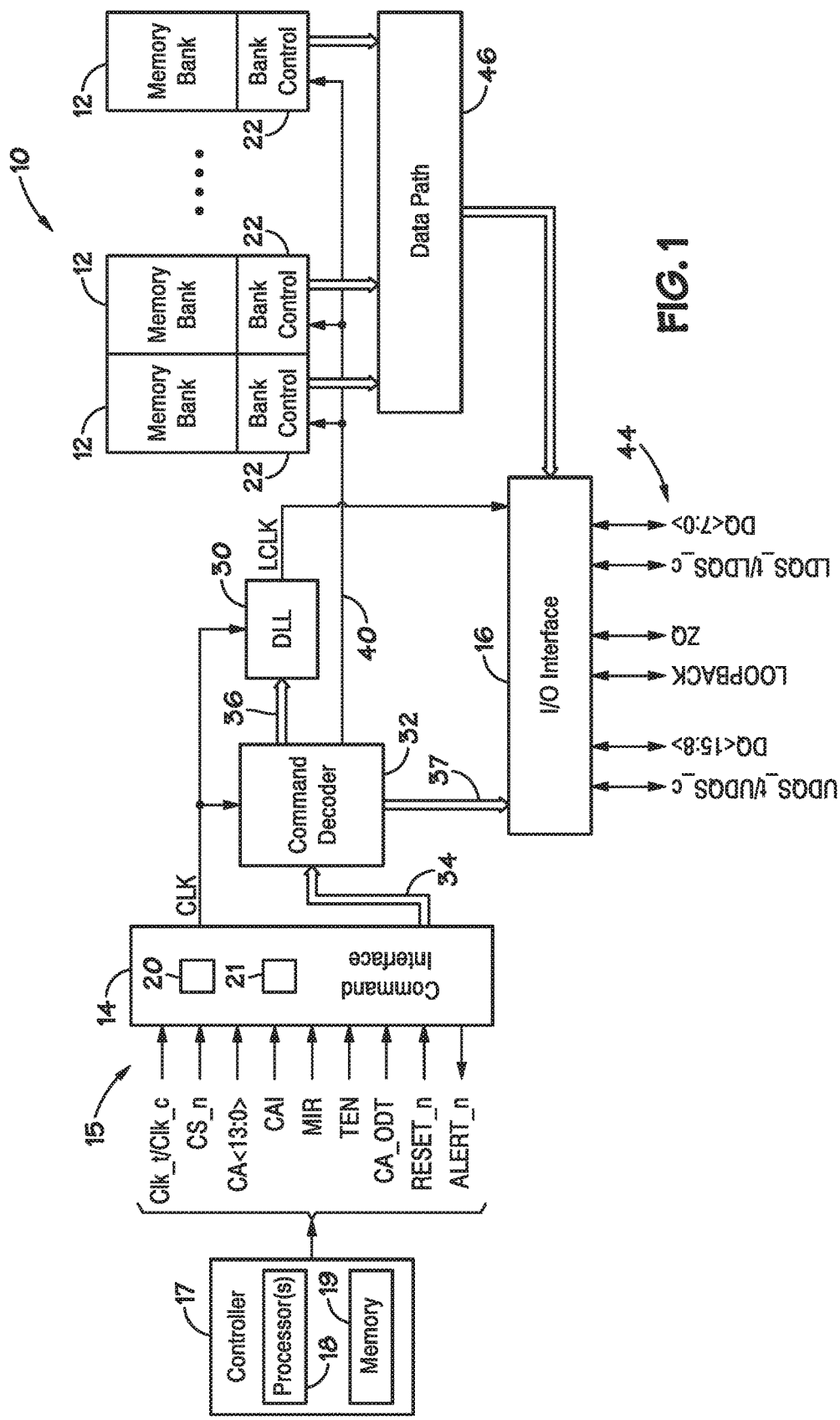
FIG. 1 is a simplified block diagram illustrating certain features of a memory device, according to an embodiment of the present disclosure

Turning now to the figures, FIG. 1 is a simplified block diagram illustrating certain features of a semiconductor device 10 (e.g., a memory device), according to an embodiment of the present disclosure. Specifically, the block diagram of FIG. 1 is a functional block diagram illustrating certain functionality of the memory device 10. In accordance with one embodiment, the memory device 10 may be a double data rate type five synchronous dynamic random access memory (DDR5 SDRAM) device. Various features of DDR5 SDRAM allow for reduced power consumption, more bandwidth and more storage capacity compared to prior generations of DDR SDRAM. While the present disclosure uses the memory device 10 as an example, it should be understood that embodiments of the present disclosure are envisioned to apply to any suitable semiconductor device, such as integrated circuits, transistors, processors, microprocessors, and the like.

The memory device 10, may include a number of memory banks 12. The memory banks 12 may be DDR5 SDRAM memory banks, for instance. The memory banks 12 may be provided on one or more chips (e.g., SDRAM chips) that are arranged on dual inline memory modules (DIMMS). Each DIMM may include a number of SDRAM memory chips (e.g., x8 or x16 memory chips), as will be appreciated. Each SDRAM memory chip may include one or more memory banks 12. The memory device 10 represents a portion of a single memory chip (e.g., SDRAM chip) having a number of memory banks 12. For DDR5, the memory banks 12 may be further arranged to form bank groups. For instance, for an 8 gigabyte (Gb) DDR5 SDRAM, the memory chip may include 16 memory banks 12, arranged into 8 bank groups, each bank group including 2 memory banks. For a 16 Gb DDR5 SDRAM, the memory chip may include 32 memory banks 12, arranged into 8 bank groups, each bank group including 4 memory banks, for instance. Various other configurations, organization and sizes of the memory banks 12 on the memory device 10 may be utilized depending on the application and design of the overall system.

The memory device 10 may include a command interface 14 and an input/output (I/O) interface 16. The command interface 14 may include processing and/or interface circuitry configured to provide a number of signals (e.g., signals 15) from an external device, such as a controller 17. The controller 17 may include processing circuitry, such as one or more processors 18 (e.g., one or more microprocessors), that may execute software programs to, for example, provide various signals 15 to the memory device 10 to facilitate the transmission and receipt of data to be written to or read from the memory device 10. Moreover, the processor(s) 18 may include multiple microprocessors, one or more "general-purpose" microprocessors, one or more special-purpose microprocessors, and/or one or more application specific integrated circuits (ASICS), or some combination thereof. For example, the processor(s) 18 may include one or more reduced instruction set (RISC) processors. The controller 17 may couple to one or more memories 19 that may store information such as control logic and/or software, look up tables, configuration data, etc. In some embodiments, the processor(s) 18 and/or the memory 19 may be external to the controller 17. The memory 19 may include a tangible, non-transitory, machine-readable-medium, such as a volatile memory (e.g., a random access memory (RAM)) and/or a nonvolatile memory (e.g., a read-only memory (ROM), flash memory, a hard drive, or any other suitable optical, magnetic, or solid-state storage medium, or a combination thereof). The memory 19 may store a variety of information and may be used for various purposes. For example, the memory 19 may store machine-readable and/or processor-executable instructions (e.g., firmware or software) for the processor(s) 18 to execute, such as instructions for providing various signals 15 to the memory device 10 to facilitate the transmission and receipt of data to be written to or read from the memory device 10. As such, the controller 17 may provide various signals 15 to the memory device 10 to facilitate the transmission and receipt of data to be written to or read from the memory device 10.

As will be appreciated, the command interface 14 may include a number of circuits, such as a clock input circuit 20 and a command address input circuit 21, for instance, to ensure proper handling of the signals 15. The command interface 14 may receive one or more clock signals from an external device. Generally, double data rate (DDR) memory utilizes a differential pair of system clock signals, referred to herein as the true clock signal (Clk_t/) and the complementary clock signal (Clk_c). The positive clock edge for DDR refers to the point where the rising true clock signal Clk_t/ crosses the falling complementary clock signal Clk_c, while the negative clock edge indicates that transition of the falling true clock signal Clk_t and the rising of the complementary clock signal Clk_c. Commands (e.g., read command, write command, etc.) are typically entered on the positive edges of the clock signal and data is transmitted or received on both the positive and negative clock edges.

The I/O interface 16 may include processing and/or interface circuitry configured to manage and/or perform input/output operations between the memory device 10 and any suitable external device coupled to the I/O interface 16.

The clock input circuit 20 receives the true clock signal (Clk_t/) and the complementary clock signal (Clk_c) and generates an internal clock signal CLK. The internal clock signal CLK is supplied to an internal clock generator, such as a delay locked loop (DLL) circuit 30. The DLL circuit 30 generates a phase controlled internal clock signal LCLK based on the received internal clock signal CLK. The phase controlled internal clock signal LCLK is supplied to the I/O interface 16, for instance, and is used as a timing signal for determining an output timing of read data.

The internal clock signal CLK may also be provided to various other components within the memory device 10 and may be used to generate various additional internal clock signals. For instance, the internal clock signal CLK may be provided to a command decoder 32. The command decoder 32 may receive command signals from the command bus 34 and may decode the command signals to provide various internal commands. For instance, the command decoder 32 may provide command signals to the DLL circuit 30 over the bus 36 to coordinate generation of the phase controlled internal clock signal LCLK. The command decoder 32 may also provide command signals to the 110 interface 16 over bus 37 to facilitate receiving and transmitting IO signals. The phase controlled internal clock signal LCLK may be used to clock data through the IO interface 16, for instance.

Further, the command decoder 32 may decode commands, such as read commands, write commands, mode-register set commands, activate commands, etc., and provide access to a particular memory bank 12 corresponding to the command, via the bus path 40. As will be appreciated, the memory device 10 may include various other decoders, such as row decoders and column decoders, to facilitate access to the memory banks 12. In one embodiment, each memory bank 12 includes a bank control block 22 which provides the necessary decoding (e.g., row decoder and column decoder), as well as other features, such as timing control and data control, to facilitate the execution of commands to and from the memory banks 12.

The memory device 10 executes operations, such as read commands and write commands, based on the command/address signals received from an external device, such as a processor. In one embodiment, the command/address bus may be a 14-bit bus to accommodate the command/address signals (CA<13:0>). The command/address signals are clocked to the command interface 14 using the clock signals (Clk_t/ and Clk_c). The command interface may include a command address input circuit 21 which is configured to receive and transmit the commands to provide access to the memory banks 12, through the command decoder 32, for instance. In addition, the command interface 14 may receive a chip select signal (CS_n). The CS_n signal enables the memory device 10 to process commands on the incoming CA<13:0>bus. Access to specific banks 12 within the memory device 10 is encoded on the CA<13:0>bus with the commands.

In addition, the command interface 14 may be configured to receive a number of other command signals. For instance, a command/address on die termination (CA_ODT) signal may be provided to facilitate proper impedance matching within the memory device 10. A reset command (RESET_n) may be used to reset the command interface 14, status registers, state machines and the like, during power-up for instance. The command interface 14 may also receive a command/address invert (CAI) signal which may be provided to invert the state of command/address signals CA<13:0>on the command/address bus, for instance, depending on the command/address routing for the particular memory device 10. A mirror (MIR) signal may also be provided to facilitate a mirror function. The MIR signal may be used to multiplex signals so that they can be swapped for enabling certain routing of signals to the memory device 10, based on the configuration of multiple memory devices in a particular application. Various signals to facilitate testing of the memory device 10, such as the test enable (TEN) signal, may be provided, as well. For instance, the TEN signal may be used to place the memory device 10 into a test mode for connectivity testing.

The command interface 14 may also be used to provide an alert signal (ALERT_n) to the system processor or controller for certain errors that may be detected. For instance, an alert signal (ALERT_n) may be transmitted from the memory device 10 if a cyclic redundancy check (CRC) error is detected. Other alert signals may also be generated. Further, the bus and pin for transmitting the alert signal (ALERT_n) from the memory device 10 may be used as an input pin during certain operations, such as the connectivity test mode executed using the TEN signal, as described above.

Data may be sent to and from the memory device 10, utilizing the command and clocking signals discussed above, by transmitting and receiving data signals 44 through the IO interface 16. More specifically, the data may be sent to or retrieved from the memory banks 12 over the data path 46, which may include multiple data paths or bi-directional data buses. Data IO signals, generally referred to as DQ signals, are generally transmitted and received in one or more bi-directional data busses. For certain memory devices, such as a DDR5 SDRAM memory device, the IO signals may be divided into upper and lower bytes. For instance, for a x16 memory device, the IO signals may be divided into upper and lower IO signals (e.g., DQ<15:8>and DQ<7:0>) corresponding to upper and lower bytes of the data signals, for instance.

To allow for higher data rates within the memory device 10, certain memory devices, such as DDR memory devices may utilize data strobe signals, generally referred to as DQS signals. The DQS signals are driven by the external processor or controller sending the data (e.g., for a write command) or by the memory device 10 (e.g., for a read command). For read commands, the DQS signals are effectively additional data output (DQ) signals with a predetermined pattern. For write commands, the DQS signals are used as clock signals to capture the corresponding input data. As with the clock signals (Clk_t/ and Clk_c), the data strobe (DQS) signals may be provided as a differential pair of data strobe signals (DQS_t/ and DQS_c) to provide differential pair signaling during reads and writes. For certain memory devices, such as a DDR5 SDRAM memory device, the differential pairs of DQS signals may be divided into upper and lower data strobe signals (e.g., UDQS_t/ and UDQS_c; LDQS_t/ and LDQS_c) corresponding to upper and lower bytes of data sent to and from the memory device 10, for instance.

An impedance (ZQ) calibration signal may also be provided to the memory device 10 through the IO interface 16. The ZQ calibration signal may be provided to a reference pin and used to tune output drivers and ODT values by adjusting pull-up and pull-down resistors of the memory device 10 across changes in process, voltage and temperature (PVT) values. Because PVT characteristics may impact the ZQ resistor values, the ZQ calibration signal may be provided to the ZQ reference pin to be used to adjust the resistance to calibrate the input impedance to known values. As will be appreciated, a precision resistor is generally coupled between the ZQ pin on the memory device 10 and GND/VSS external to the memory device 10. This resistor acts as a reference for adjusting internal ODT and drive strength of the IO pins.

In addition, a loopback signal (LOOPBACK) may be provided to the memory device 10 through the IO interface 16. The loopback signal may be used during a test or debugging phase to set the memory device 10 into a mode wherein signals are looped back through the memory device 10 through the same pin. For instance, the loopback signal may be used to set the memory device 10 to test the data output (DQ) of the memory device 10. Loopback may include both a data and a strobe or possibly just a data pin. This is generally intended to be used to monitor the data captured by the memory device 10 at the IO interface 16.

As will be appreciated, various other components such as power supply circuits (for receiving external VDD and VSS signals), mode registers (to define various modes of programmable operations and configurations), read/write amplifiers (to amplify signals during read/write operations), temperature sensors (for sensing temperatures of the memory device 10), etc., may also be incorporated into the memory system 10. Accordingly, it should be understood that the block diagram of FIG. 1 is only provided to highlight certain functional features of the memory device 10 to aid in the subsequent detailed description.

Figure 2:
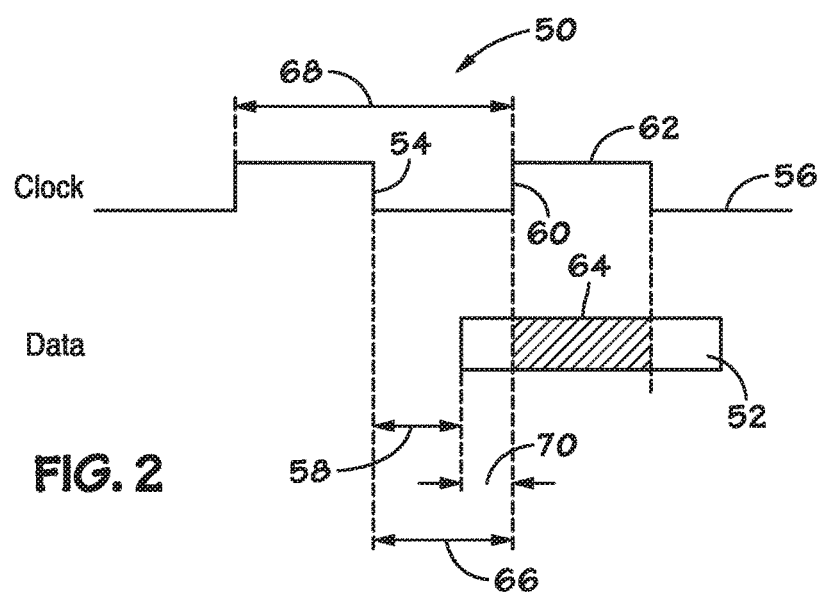
FIG. 2 is an example timing diagram for reading data on a data path of the memory device of FIG. 1 in a low frequency domain.

With the foregoing in mind, FIG. 2 is an example timing diagram 50 for reading data 52 on a data path 46 of the memory device 10 of FIG. 1 in a low frequency domain. At a falling edge 54 of a clock signal 56, the data 52 may be instructed to be sent on the data path 46. In some embodiments, the clock signal 56 may include the phase controlled internal clock signal generated by the DLL circuit 30, LCLK. However, there may be an output delay 58 between the falling edge 54 of the clock signal 56 and when the data 52 is on the data path 46. The output delay 58 (e.g., a CLK-to-Q time) may be associated with a time to output the data 52 to the data path 46. In particular, the output delay 58 may be associated with the time it takes for logic in or coupled to the data path 46 to output the data 52 to the data path 46.

At a next rising edge 60 of the clock signal 56, the data path 46 may be captured and output from the memory device 10. The data path 46 may be captured while the clock signal 56 is high 62. As such, the shaded portion 64 of the data 52 is captured and output from the memory device 10.

A read delay 66 is measured between the falling edge 54 of the clock signal 56 (e.g., when the data 52 may be instructed to be sent on the data path 46) and the next rising edge 60 of the clock signal 56 (e.g., when the data path 46 may be captured and output from the memory device 10). As such, the read delay 66 is one half of a period 68 (i.e., tCK) 68 of the clock signal 56, or ½ tCK.

A remaining or logic time 70, i.e., the read delay 66 minus the output delay time 58, may be used to perform functions programmed into logic in or coupled to the data path 46. The logic (which may include a combination of different kinds of logic) may perform programmed instructions based on the data 52. For example, the logic may convert the data 52, which may be in parallel data format when stored in an array (e.g., of one or more memory banks 12), to a serial data format. Additionally or alternatively, the logic may combine the data with one or more clocking signals, such as a clock-timed, DLL-domain, shifted signal, such that the data 52 is synchronous with the phase controlled internal clock signal generated by the DLL circuit 30, LCLK. As such, the output data (e.g., the associated DQ signal 44) may be aligned with LCLK.

However, in some high frequency domains, at least some of the data output from the data path 46 may not be the data 52, resulting in no data or the wrong data being output from the memory device 10. This may be due to the output delay 58 associated with outputting the data 52 on the data path 46 being greater than the remaining or logic time 70. As an example, there may be three gates in or coupled to the data path 46 to output the data 52 to the data path 46, and each gate may have a delay of 60 ps (picoseconds). As such, the output delay 58 is 180 ps (i.e., 3×60 ps). In certain applications, and as shown in the example timing diagram 50 of FIG. 2, the read delay 66 (i.e., one half of a period 68 of the clock signal 56) is greater than the output delay 58, and therefore the data output from the data path 46 is the requested (e.g., correct) data 52. In other words, when the period 68 of the clock signal 56 is less than double the duration of the output delay 58, the data 64 may be pushed into a next cycle of the clock potentially causing incorrect output data to be output from the memory device 10. However, when the frequency of the clock signal 56 is sufficiently high, such that the read delay 66 is less than the output delay 58, no data or the wrong data may be output from the memory device 10.

Figure 3:
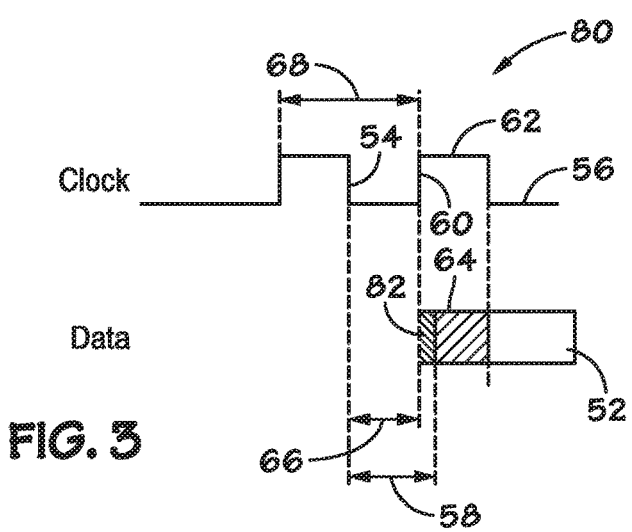
FIG. 3 is an example timing diagram for reading data on a data path of the memory device of FIG. 1 in a high frequency domain.

FIG. 3 is an example timing diagram 80 for reading data 52 on a data path 46 of the memory device 10 of FIG. 1 in a high frequency domain, such as when using a DDR5 SDRAM memory device. For example, the high frequency domain may be greater or equal to 1.66 GHz (gigahertz), 2 GHz, 2.5 GHz, and the like. In particular, the frequency of the clock signal 56 is sufficiently high such that the read delay 66 (i.e., one half of the period 68 of the clock signal 56) is less than the output delay 58.

At a falling edge 54 of a clock signal 56, the data 52 may be instructed to be sent on the data path 46. There may be an output delay 58 between the falling edge 54 of the clock signal 56 and when the data 52 is on the data path 46.

At a next rising edge 60 of the clock signal 56, the data path 46 may be captured and output from the memory device 10. The data path 46 may be captured while the clock signal 56 is high 62. However, because the read delay 66 (i.e., one half of the period 68 of the clock signal 56) is less than the output delay 58, at least a portion 82 of the data path 46 that is captured does not include the data 52 (e.g., is no data or incorrect data). After the output delay 58, the shaded portion 64 of the requested data 52 is captured. This combination of no data or incorrect data 82 and the requested data 52 may then be output from the memory device 10.

Figure 4:
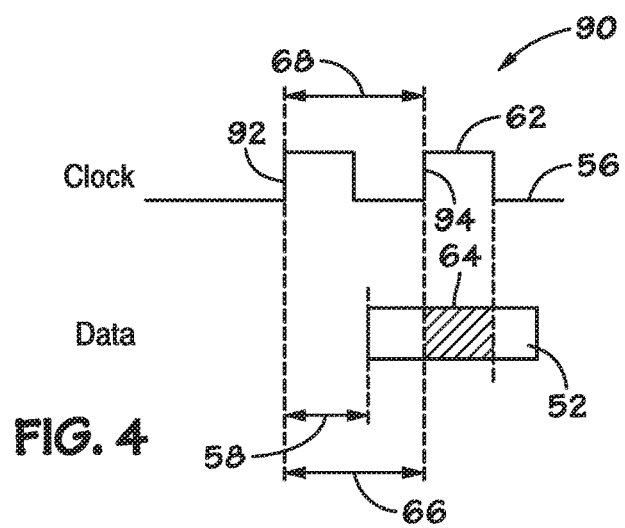
FIG. 4 is an example timing diagram for reading data on a data path of the memory device of FIG. 1 in a high frequency domain, wherein a read delay is approximately equal to a period of an input clock signal, according to an embodiment of the present disclosure.

To ensure that the requested data 52 is captured, the read delay 66 may be increased such that it is greater or equal to the output delay 58 (e.g., such that it is approximately equal to the period 68 of the clock signal 56). While the present disclosure uses the example of the read delay 66 being approximately equal to the period 68 of the clock signal 56, it should be understood that any suitable read delay 66 that is greater or equal to the output delay 58 is contemplated. FIG. 4 is an example timing diagram 90 for reading data 52 on a data path 46 of the memory device 10 of FIG. 1 in a high frequency domain, wherein the read delay 66 is approximately equal to the period 68 (e.g., 1*tCK) of the clock signal 56, according to an embodiment of the present disclosure.

At a first rising edge 92 of a clock signal 56, the data 52 may be instructed to be sent on the data path 46. There may be an output delay 58 between the falling edge 54 of the clock signal 56 and when the data 52 is on the data path 46.

At a next rising edge 94 of the clock signal 56, the data path 46 may be captured and output from the memory device 10. The data path 46 may be captured while the clock signal 56 is high 62. Because the read delay 66 (i.e., the period 68 of the clock signal 56) is greater than the output delay 58, the shaded portion 64 of the data 52 that is captured and output from the memory device 10 includes data that is not incorrect data. In this manner, increasing the read delay 66 such that it is greater or equal to the output delay 58 (e.g., such that it is approximately equal to the period 68 of the clock signal 56) may ensure that the requested data 52 is captured.

Figure 5:
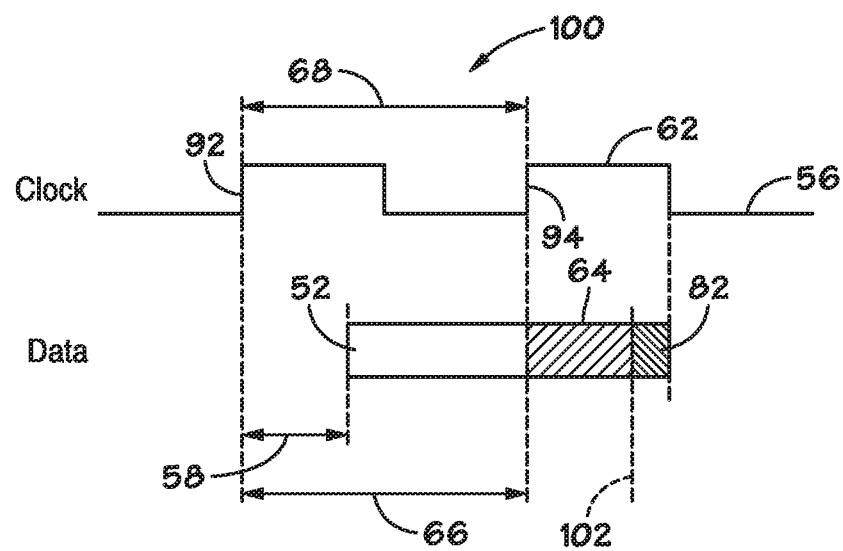
FIG. 5 is an example timing diagram for reading data on a data path of the memory device of FIG. 1 in a lower frequency domain, wherein a read delay is approximately equal to a period of an input clock signal, according to an embodiment of the present disclosure.

However, extending the read delay 66 in this manner may result no data or incorrect data being captured at a trailing end of the data 52 rather than a leading end of the data 52 when the memory device 10 is programmed, for example, for lower frequency domains. FIG. 5 is an example timing diagram 100 for reading data 52 on a data path 46 of the memory device 10 of FIG. 1 in a lower frequency domain, wherein the read delay 66 is approximately equal to the period 68 of the clock signal 56, according to an embodiment of the present disclosure. For example, the lower frequency domain may be less than or equal to 1.66 GHz, 1.5 GHz, 1.25 GHz, and the like. In particular, the frequency of the clock signal 56 is sufficiently low such that an end 102 of the data 52 is captured via the data path 46 and output from the memory device 10 when the clock signal 56 is high 62, but before the clock signal 56 transitions to low.

At a first rising edge 92 of a clock signal 56, the data 52 may be instructed to be sent on the data path 46. There may be an output delay 58 between the first rising edge 92 of the clock signal 56 and when the data 52 is on the data path 46.

At a next rising edge 94 of the clock signal 56, the data path 46 may be captured and output from the memory device 10. The data path 46 may be captured while the clock signal 56 is high 62. As such, the shaded portion 64 of the requested data 52 is captured. However, because the end 102 of the data 52 occurs while the data path 46 is being captured and output from the memory device 10 (e.g., when the clock signal 56 is high 62), at least a portion 82 of the data path 46 that is captured does not include the data 52 (e.g., is no data or incorrect data). This combination of requested data 52 and no data or incorrect data 82 may then be output from the memory device 10.

Figure 6:
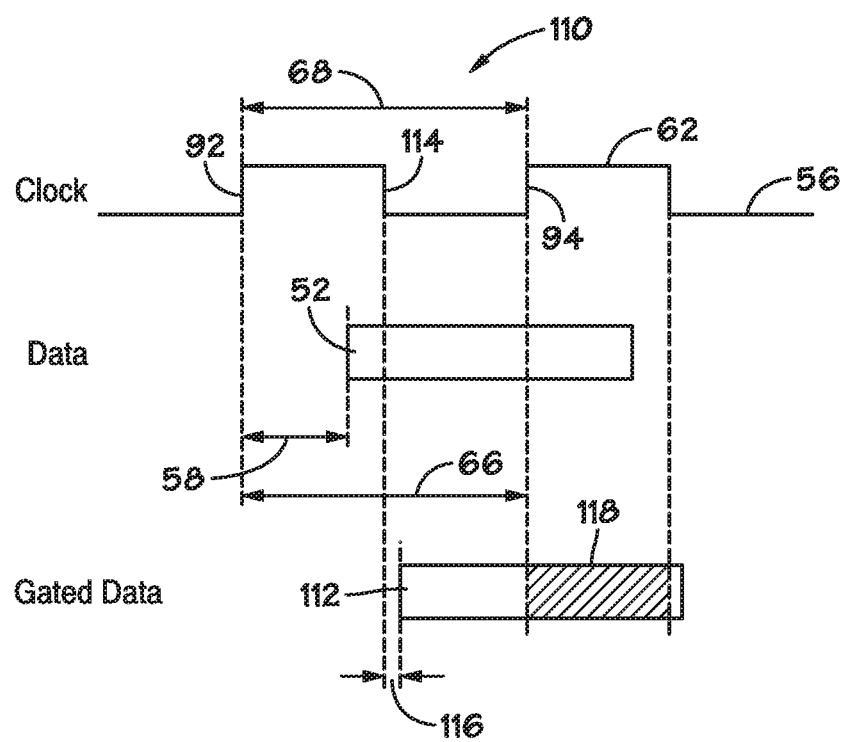
FIG. 6 is an example timing diagram for reading gated data on a data path of the memory device of FIG. 1 in a lower frequency domain, wherein a read delay is approximately equal to a period of an input clock signal, according to an embodiment of the present disclosure.

To ensure that the requested data 52 is captured, the data path 46 may be gated such that the requested data 52 in the data path 46 may be stored and read while the clock signal is high (e.g., at 62). FIG. 6 is an example timing diagram 110 for reading gated data 112 on a data path 46 of the memory device 10 of FIG. 1 in a lower frequency domain, wherein the read delay 66 is approximately equal to the period 68 of the clock signal 56, according to an embodiment of the present disclosure.

At a first rising edge 92 of a clock signal 56, the data 52 may be instructed to be sent on the data path 46. There may be an output delay 58 between the first rising edge 92 of the clock signal 56 and when the data 52 is on the data path 46.

At a next falling edge 114 of the clock signal 56, a latch coupled to the data path 46 may be instructed to gate the data path 46. As such, after a latch delay 116, the latch may gate the data 52 in the data path 46, generating gated data 112.

At a next rising edge 94 of the clock signal 56, a shaded portion 118 of the gated data 112 may be captured and output from the memory device 10. The gated data 112 may be captured while the clock signal 56 is high 62. Gating the data path 46 may ensure that the requested data 52 in the data path 46 is captured and read while the clock signal is high (e.g., at 62). Moreover, systems, devices, methods, and the like, implementing the example timing diagram 110 may be used in high frequency domains as well as lower frequency domains, with appropriate results independent of frequency as seen in the example timing diagram 90 of FIG. 4.

Figure 7:
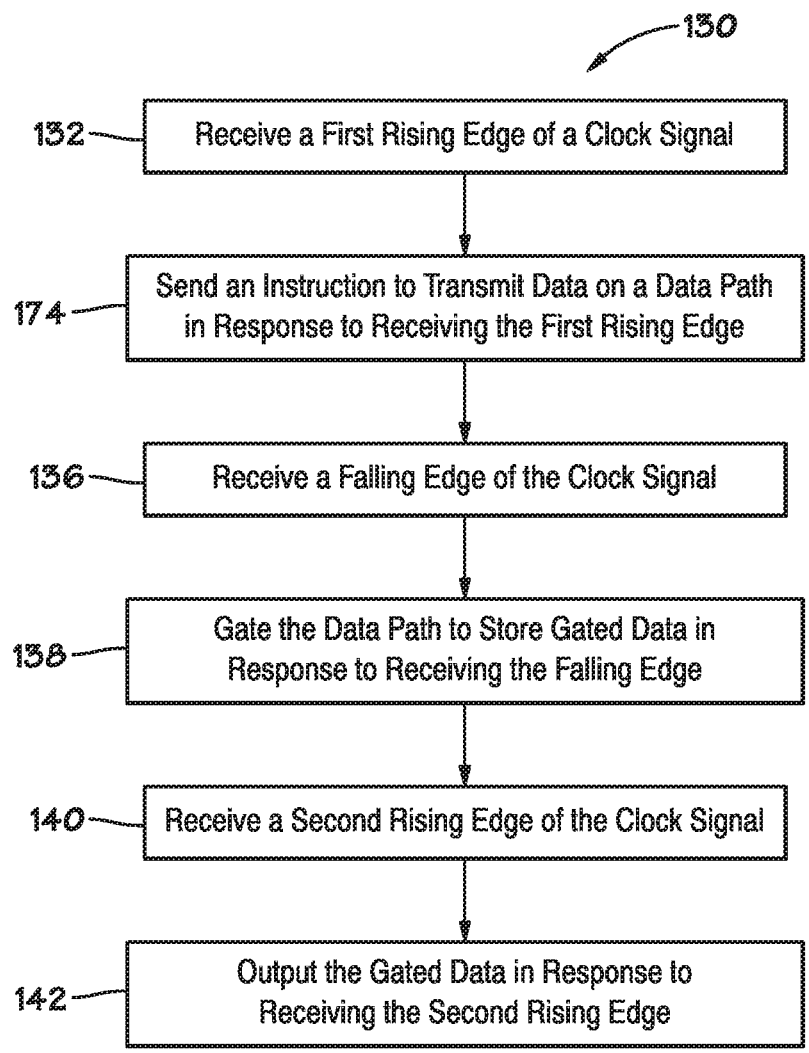
FIG. 7 is a flow diagram of a method for ensuring that requested data in a data path is captured and output by the memory device of FIG. 1, wherein a read delay is approximately equal to a period of an input clock signal, according to an embodiment of the present disclosure.

FIG. 7 is a flow diagram of a method 130 for ensuring that the requested data 52 in the data path 46 is captured and output by the memory device 10 of FIG. 1 even when the read delay 66 is greater than half the period 68 (e.g., approximately equal to the period 68) of the clock signal 56, according to an embodiment of the present disclosure. In particular, performing the method 130 may result in the example timing diagram 110 of FIG. 6. The method 130 may be performed by any suitable device or combination of devices that may send an instruction to transmit data 52 on a data path 46 of a semiconductor device in response to receiving a first rising edge 92 of a clock signal 56 in the semiconductor device, gate the data path 46 to store gated data 112 in response to receiving a falling edge 114 of the clock signal 56, and output the gated data 112 in response to receiving a second rising edge 94 of the clock signal 56. While the method 130 is described using steps in a specific sequence, it should be understood that the present disclosure contemplates that the described steps may be performed in different sequences than the sequence illustrated, and certain described steps may be skipped or not performed altogether. In some embodiments, at least some of the steps of the method 130 may be performed by a command interface 14 and/or an input/output (I/O) interface 16 of the semiconductor device (e.g., the memory device 10). As such, the method 130 is described below as being performed by the I/O interface 16. However, it should be understood that any suitable device or combination of devices is contemplated to perform the method 130, such as a controller (e.g., a memory bank controller, the controller 17 coupled to the semiconductor device, and the like).

As illustrated, the I/O interface 16 receives (process block 132) a first rising edge 92 of the clock signal 56. In response to receiving the first rising edge 92, the I/O interface 16 sends (process block 134) an instruction (e.g., to one or more memory banks 12) to transmit data 52 on the data path 46. There may be an output delay 58 between the first rising edge 92 of the clock signal 56 and when the data 52 is on the data path 46.

The I/O interface 16 then receives (process block 136) a falling edge (e.g., the next falling edge 114) of the clock signal 56. In response to receiving the next falling edge 114, the I/O interface 16 gates (process block 138) the data path 46 to store gated data 112. In particular, the I/O interface 16 may store the data 52 on the data path 46 in a latch after a latch delay 116.

The I/O interface 16 receives (process block 140) a second rising edge (e.g., the next rising edge 94) of the clock signal 56. In response to receiving the second rising edge 94, the I/O interface 16 outputs (process block 142) the gated data 112 (e.g., the shaded portion 118 of the gated data 112). In particular, the I/O interface 16 may read the data 118 and output the data 118 from the memory device 10.

As such, the time (i.e., the read delay 66) between sending the instruction to transmit requested data 52 on the data path 46 (e.g., at the first rising edge 92) and beginning to output the gated data 118 is a period 68 of the clock signal 56. The period 68 of the clock signal 56 may be greater or equal to an output delay 58 associated with sending the requested data 52 on the data path 46, thus preventing no data or wrong data from being read in high frequency domains. Moreover, gating the data path 46 may ensure that the requested data 52 is outputted for lower frequency domains. In this manner, the requested data 52 may be properly output from the memory device 10.

Figure 8:
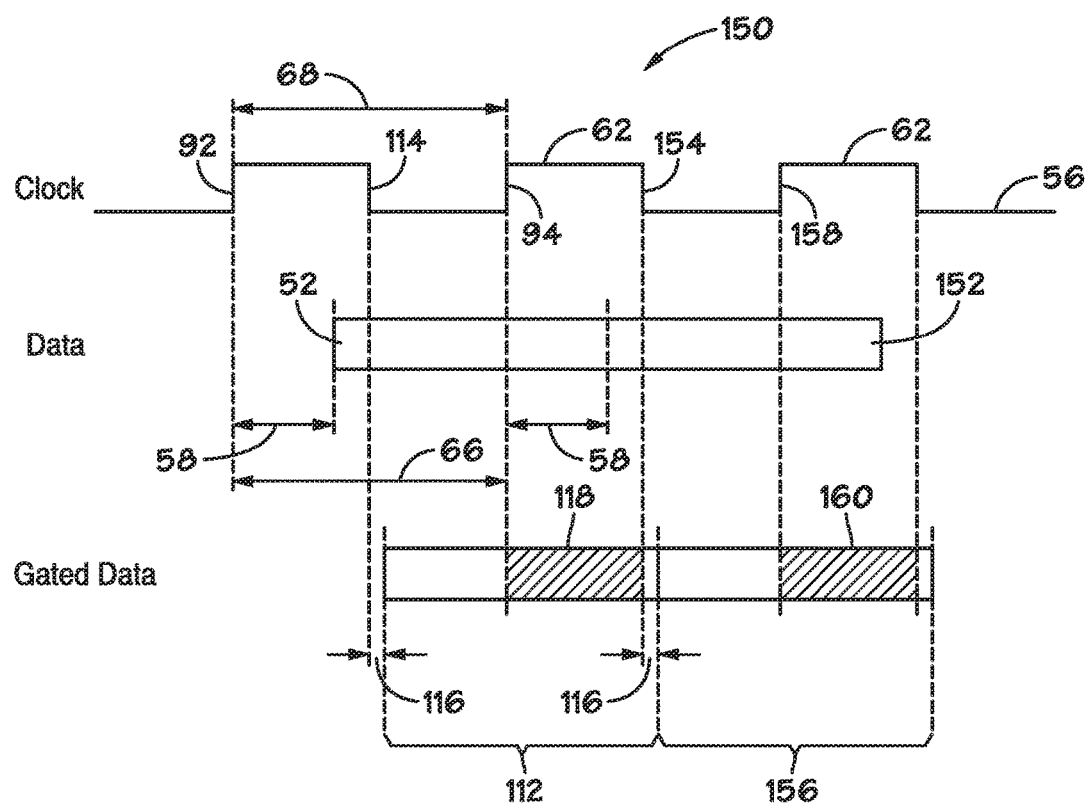
FIG. 8 is an example timing diagram for reading multiple sets of gated data (e.g., multiple gated data words) on a data path of the memory device of FIG. 1 in a lower frequency domain, wherein a read delay is approximately equal to a period of an input clock signal, according to an embodiment of the present disclosure.

In certain cases, multiple (consecutive) sets of data (e.g., data words) may be requested from and output by the memory device 10. FIG. 8 is an example timing diagram 150 for reading multiple sets of gated data 112 (e.g., multiple gated data words) on a data path 46 of the memory device 10 of FIG. 1 using a single clock in a lower frequency domain, wherein the read delay 66 is approximately equal to the period 68 of the clock signal 56, according to an embodiment of the present disclosure.

At a first rising edge 92 of a clock signal 56, first data 52 may be instructed to be sent on the data path 46. There may be an output delay 58 between the first rising edge 92 of the clock signal 56 and when the first data 52 is on the data path 46.

At a next falling edge 114 of the clock signal 56, a first latch coupled to the data path 46 may be instructed to gate the data path 46. As such, after a latch delay 116, the first latch may gate the first data 52 in the data path 46, generating first gated data 112.

At a next rising edge 94 of the clock signal 56, a first shaded portion 118 of the first gated data 112 may be captured and output from the memory device 10. The first gated data 112 may be captured while the clock signal 56 is high 62. Additionally, second data 152 may also be instructed to be sent on the data path 46 at the next rising edge 94. There may be an output delay 58 between the next rising edge 94 of the clock signal 56 and when the second data 152 is on the data path 46.

At a next falling edge 154 of the clock signal 56, the latch may be instructed to gate the data path 46. As such, after the latch delay 116, the latch may gate the second data 152 in the data path 46, generating second gated data 156. In some embodiments, a second latch may additionally or alternatively be instructed to gate the data path 46.

At a next rising edge 158 of the clock signal 56, a second shaded portion 160 of the gated data 156 may be captured and output from the memory device 10. The second gated data 156 may be captured while the clock signal 56 is high 62. Systems, devices, methods, and the like, implementing the example timing diagram 150 may be used in high frequency domains as well as lower frequency domains. In this manner, multiple (consecutive) sets of data (e.g., data words) may be requested from and output by the memory device 10.

Figure 9:
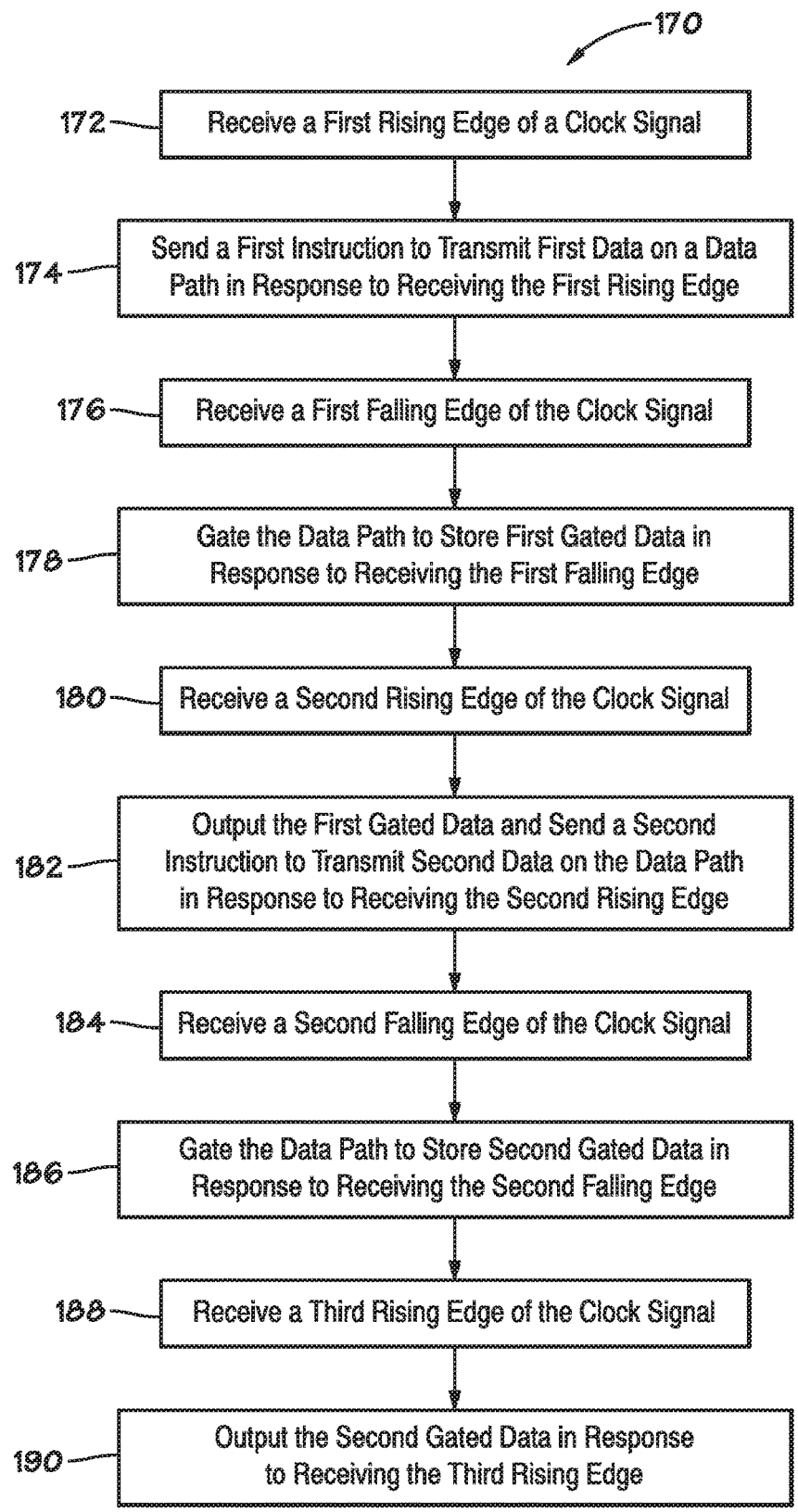
FIG. 9 is a flow diagram of a method for ensuring that multiple sets of requested data (e.g., requested data words) in a data path are captured and output by the memory device of FIG. 1, wherein a read delay is approximately equal to a period of an input clock signal, according to an embodiment of the present disclosure.

FIG. 9 is a flow diagram of a method 170 for ensuring that multiple sets of requested data (e.g., requested data words) in the data path 46 are captured and output by the memory device 10 of FIG. 1, wherein the read delay 66 is approximately equal to the period 68 of the clock signal 56, according to an embodiment of the present disclosure. In particular, performing the method 170 may result in the example timing diagram 150 of FIG. 8. The method 170 may be performed by any suitable device or combination of devices that may at least send an instruction to transmit data 52 on a data path 46 of a semiconductor device in response to receiving a first rising edge 92 of a clock signal 56 in the semiconductor device, gate the data path 46 to store gated data 112 in response to receiving a falling edge 114 of the clock signal 56, and output the gated data 112 in response to receiving a second rising edge 94 of the clock signal 56. While the method 170 is described using steps in a specific sequence, it should be understood that the present disclosure contemplates that the described steps may be performed in different sequences than the sequence illustrated, and certain described steps may be skipped or not performed altogether. In some embodiments, at least some of the steps of the method 170 may be performed by a command interface 14 and/or an input/output (I/O) interface 16 of the semiconductor device (e.g., the memory device 10). As such, the method 170 is described below as being performed by the I/O interface 16. However, it should be understood that any suitable device or combination of devices is contemplated to perform the method 170, such as a controller (e.g., a memory bank controller, the controller 17 coupled to the semiconductor device, and the like).

As illustrated, the I/O interface 16 receives (process block 172) a first rising edge 92 of the clock signal 56. In response to receiving the first rising edge 92, the I/O interface 16 sends (process block 174) an instruction (e.g., to one or more memory banks 12) to transmit first data 52 on the data path 46. There may be an output delay 58 between the first rising edge 92 of the clock signal 56 and when the first data 52 is on the data path 46.

The I/O interface 16 then receives (process block 176) a first falling edge (e.g., the next falling edge 114) of the clock signal 56. In response to receiving the next falling edge 114, the I/O interface 16 gates (process block 178) the data path 46 to store first gated data 112. In particular, the I/O interface 16 may store the first data 52 on the data path 46 in a latch after a latch delay 116.

The I/O interface 16 receives (process block 180) a second rising edge (e.g., the next rising edge 94) of the clock signal 56. In response to receiving the second rising edge 94, the I/O interface 16 outputs (process block 182) the first gated data 112 (e.g., a first shaded portion 118 of the first gated data 112) and sends a second instruction (e.g., to one or more memory banks 12) to transmit second data 152 on the data path 46. In particular, the I/O interface 16 may read the data 118 and output the data 118 from the memory device 10. There may be an output delay 58 between the second rising edge 94 of the clock signal 56 and when the second data 152 is on the data path 46.

The I/O interface 16 then receives (process block 184) a second falling edge (e.g., the next falling edge 154) of the clock signal 56. In response to receiving the second falling edge 154, the I/O interface 16 gates (process block 186) the data path 46 to store second gated data 156. In particular, the I/O interface 16 may store the data 152 on the data path 46 in the latch after the latch delay 116.

The I/O interface 16 receives (process block 188) a third rising edge (e.g., the next rising edge 158) of the clock signal 56. In response to receiving the third rising edge 158, the I/O interface 16 outputs (process block 190) the second gated data 156 (e.g., the second shaded portion 160 of the second gated data 156). In particular, the I/O interface 16 may read the second data 160 and output the third from the memory device 10. As such, the method 170 may capture and output multiple sets of requested data 52, 152 in the data path 46 from the memory device 10, wherein the read delay 66 is approximately equal to the period 68 of the clock signal 56.

Figure 10:
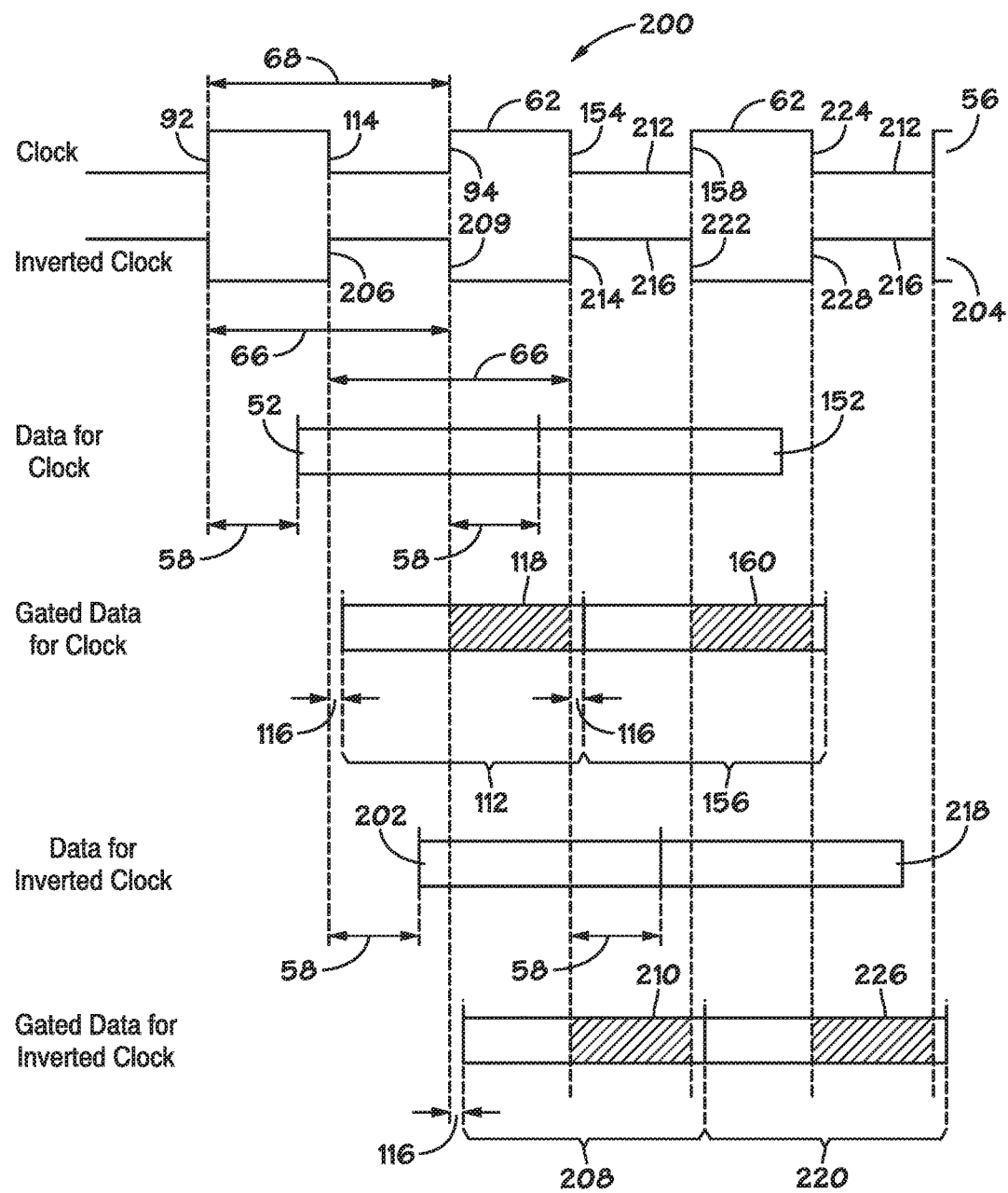
FIG. 10 is an example timing diagram for reading multiple sets of gated data on multiple data paths of the memory device of FIG. 1 based on rising and falling edges of the clock signal in a lower frequency domain, wherein a read delay is approximately equal to a period of an input clock signal, according to an embodiment of the present disclosure.

In some embodiments, multiple sets of data (e.g., data words) may be requested from and output by the memory device 10 via multiple data paths 46 based on rising and falling edges of the clock signal 56, or the clock signal 56 and an inverted clock signal. FIG. 10 is an example timing diagram 200 for reading multiple sets of gated data (e.g., multiple gated data words) on multiple data paths 46 of the memory device 10 of FIG. 1 based on rising and falling edges of the clock signal 56 in a lower frequency domain, wherein the read delay 66 is approximately equal to the period 68 of the clock signal 56, according to an embodiment of the present disclosure.

At a first rising edge 92 of a clock signal 56, first data 52 may be instructed to be sent on a first data path 46. There may be an output delay 58 between the first rising edge 92 of the clock signal 56 and when the first data 52 is on the first data path 46.

At a next falling edge 114 of the clock signal 56, a first latch coupled to the data path 46 may be instructed to gate the data path 46. As such, after a latch delay 116, the first latch may gate the first data 52 in the data path 46, generating first gated data 112. Second data 202 may also be instructed to be sent on a second data path 46 at the next falling edge 114 of the clock signal 56. There may be an output delay 58 between the next falling edge 114 of the clock signal 56 and when the second data 202 is on the second data path 46. An inverted clock signal 204, which inverts the clock signal 56, is shown in the example timing diagram 200. It should be understood that any transmitting, receiving, and/or gating of data based on the clock signal 56 may additionally or alternatively be based on the inverted clock signal 204. As such, in some embodiments, the second data 202 may additionally or alternatively be instructed to be sent on the second data path 46 at a first rising edge 206 of the inverted clock signal 204.

At a next rising edge 94 of the clock signal 56, a first shaded portion 118 of the first gated data 112 may be captured and output from the memory device 10. The first gated data 112 may be captured while the clock signal 56 is high 62. Additionally, third data 152 may also be instructed to be sent on the first data path 46 at the next rising edge 94. There may be an output delay 58 between the next rising edge 94 of the clock signal 56 and when the third data 152 is on the first data path 46. Furthermore, a second latch coupled to the second data path 46 may be instructed to gate the second data path 46 at the next rising edge 94. As such, after the latch delay 116, the second latch may gate the second data 202 in the second data path 46, generating second gated data 208. In some embodiments, the second data path 46 may additionally or alternatively be gated in the second latch at a next falling edge 209 of the inverted clock signal 204.

At a next falling edge 154 of the clock signal 56, the first latch may be instructed to gate the data path 46. As such, after the latch delay 116, the first latch may gate the third data 152 in the first data path 46, generating third gated data 156. A second shaded portion 210 of the second gated data 208 may also be captured and output from the memory device 10 at the next falling edge 154 of the clock signal 56. The second gated data 208 may be captured while the clock signal 56 is low 212. In some embodiments, the second gated data 208 may additionally or alternatively be captured and output from the memory device 10 at a next rising edge 214 of the inverted clock signal 204. As such, the second gated data 208 may be captured while the inverted clock signal 204 is high 216. Additionally, fourth data 218 may also be instructed to be sent on the second data path 46 at the next falling edge 154 of the clock signal 56. There may be an output delay 58 between the next falling edge 154 of the clock signal 56 and when the fourth data 218 is on the second data path 46. In some embodiments, the fourth data 218 may additionally or alternatively be instructed to be sent on the second data path 46 at the next rising edge 214 of the inverted clock signal 204.

At a next rising edge 158 of the clock signal 56, a third shaded portion 160 of the third gated data 156 may be captured and output from the memory device 10. The third gated data 156 may be captured while the clock signal 56 is high 62. Additionally, the second latch coupled to the second data path 46 may be instructed to gate the second data path 46 at the next rising edge 158. As such, after the latch delay 116, the second latch may gate the fourth data 218 in the second data path 46, generating fourth gated data 220. In some embodiments, the second data path 46 may additionally or alternatively be gated in the second latch at a next falling edge 222 of the inverted clock signal 204.

At a next falling edge 224 of the clock signal 56, a fourth shaded portion 226 of the fourth gated data 220 may also be captured and output from the memory device 10. The fourth gated data 220 may be captured while the clock signal 56 is low 212. In some embodiments, the fourth gated data 220 may additionally or alternatively be captured and output from the memory device 10 at a next rising edge 228 of the inverted clock signal 204. As such, the second gated data 208 may be captured while the inverted clock signal 204 is high 216.

Systems, devices, methods, and the like, implementing the example timing diagram 200 may be used in high frequency domains as well as lower frequency domains. Additionally, while the example timing diagram 200 illustrates reading multiple sets of gated data (e.g., multiple gated data words), it should be understood that the example timing diagram 200 may also be applied to reading single sets of gated data (e.g., single gated data words). In this manner, multiple sets of data (e.g., data words) may be requested from and output by the memory device 10 via multiple data paths 46 based on rising and falling edges of the clock signal 56, or the clock signal 56 and the inverted clock signal 204.

Figure 11:
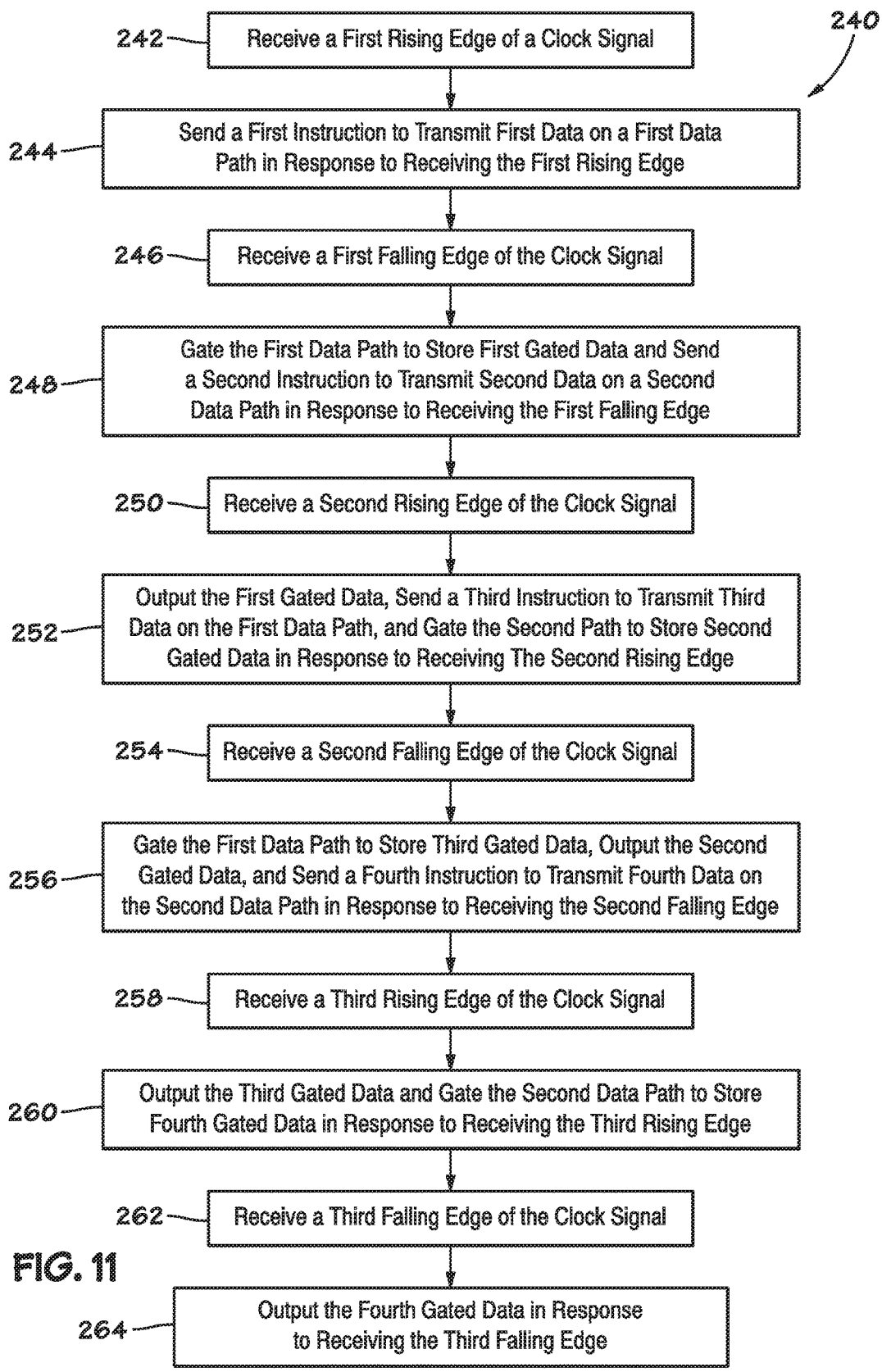
FIG. 11 is a flow diagram of a method for ensuring that multiple sets of requested data are captured and output by the memory device of FIG. 1 via multiple data paths based on rising and falling edges of an input clock signal, wherein a read delay is approximately equal to a period of the input clock signal, according to an embodiment of the present disclosure.

FIG. 11 is a flow diagram of a method 240 for ensuring that multiple sets of requested data (e.g., requested data words) are captured and output by the memory device 10 of FIG. 1 via multiple data paths 46 based on rising and falling edges of an input clock signal 56, wherein the read delay 66 is approximately equal to the period 68 of the clock signal 56, according to an embodiment of the present disclosure. In particular, performing the method 240 may result in the example timing diagram 200 of FIG. 10. The method 240 may be performed by any suitable device or combination of devices that may at least send an instruction to transmit data 52 on a data path 46 of a semiconductor device in response to receiving a first rising edge 92 of a clock signal 56 in the semiconductor device, gate the data path 46 to store gated data 112 in response to receiving a falling edge 114 of the clock signal 56, and output the gated data 112 in response to receiving a second rising edge 94 of the clock signal 56. Moreover, in some embodiments, any of the steps of the method 240 may additionally or alternatively be performed at falling or rising edges of the inverted clock signal 204. While the method 240 is described using steps in a specific sequence, it should be understood that the present disclosure contemplates that the described steps may be performed in different sequences than the sequence illustrated, and certain described steps may be skipped or not performed altogether. In some embodiments, at least some of the steps of the method 240 may be performed by a command interface 14 and/or an input/output (I/O) interface 16 of the semiconductor device (e.g., the memory device 10). As such, the method 240 is described below as being performed by the I/O interface 16. However, it should be understood that any suitable device or combination of devices is contemplated to perform the method 240, such as a controller (e.g., a memory bank controller, the controller 17 coupled to the semiconductor device, and the like).

As illustrated, the I/O interface 16 receives (process block 242) a first rising edge 92 of the clock signal 56. In response to receiving the first rising edge 92, the I/O interface 16 sends (process block 244) a first instruction (e.g., to one or more memory banks 12) to transmit first data 52 on a first data path 46. There may be an output delay 58 between the first rising edge 92 of the clock signal 56 and when the first data 52 is on the first data path 46.

The I/O interface 16 then receives (process block 246) a first falling edge (e.g., the next falling edge 114) of the clock signal 56. In response to receiving the next falling edge 114, the I/O interface 16 gates (process block 248) the first data path 46 to store first gated data 112 and sends a second instruction (e.g., to one or more memory banks 12) to transmit second data 202 on a second data path 46. In particular, the I/O interface 16 may store the first data 52 on the first data path 46 in a first latch after a latch delay 116. There may be an output delay 58 between the next falling edge 114 of the clock signal 56 and when the second data 202 is on the second data path 46. In some embodiments, the second data 202 may additionally or alternatively be instructed to be sent on the second data path 46 at a first rising edge 206 of the inverted clock signal 204.

The I/O interface 16 receives (process block 250) a second rising edge (e.g., the next rising edge 94) of the clock signal 56. In response to receiving the second rising edge 94, the I/O interface 16 outputs (process block 252) the first gated data 112 (e.g., a first shaded portion 118 of the first gated data 112), sends a third instruction (e.g., to one or more memory banks 12) to transmit third data 152 on the first data path 46, and gates the second data path 46 to store second gated data 208. In particular, the I/O interface 16 may read the data 118 and output the data 118 from the memory device 10. There may be an output delay 58 between the next rising edge 94 of the clock signal 56 and when the third data 152 is on the first data path 46. The I/O interface 16 may store the second data 202 on the second data path 46 in a second latch after the latch delay 116. In some embodiments, the second data path 46 may additionally or alternatively be gated in the second latch at a first falling edge 209 of the inverted clock signal 204.

The I/O interface 16 then receives (process block 254) a second falling edge (e.g., the next falling edge 154) of the clock signal 56. In response to receiving the second falling edge 154, the I/O interface 16 gates (process block 256) the first data path 46 to store third gated data 156, outputs the second gated data 208 (e.g., a second shaded portion 210 of the second gated data 208), and sends a fourth instruction (e.g., to one or more memory banks 12) to transmit fourth data 218 on the second data path 46. In particular, the I/O interface 16 may store the data 152 on the first data path 46 in the first latch after the latch delay 116. The I/O interface 16 may read the data 210 and output the data 210 from the memory device 10. There may be an output delay 58 between the second falling edge 154 of the clock signal 56 and when the fourth data 218 is on the second data path 46. In some embodiments, the second gated data 208 may additionally or alternatively be captured and output from the memory device 10 at a second rising edge 214 of the inverted clock signal 204. Similarly, the fourth data 218 may additionally or alternatively be instructed to be sent on the second data path 46 at the second rising edge 214 of the inverted clock signal 204.

The I/O interface 16 receives (process block 258) a third rising edge (e.g., the next rising edge 158) of the clock signal 56. In response to receiving the third rising edge 158, the I/O interface 16 outputs (process block 260) the third gated data 156 (e.g., the third shaded portion 160 of the third gated data 156) and gates the second data path 46 to store fourth gated data 220. In particular, the I/O interface 16 may read the third data 160 and output the third data 160 from the memory device 10. The I/O interface 16 may also store the fourth data 218 on the second data path 46 in the second latch after the latch delay 116. In some embodiments, the second data path 46 may additionally or alternatively be gated in the second latch at a second falling edge 222 of the inverted clock signal 204.

The I/O interface 16 then receives (process block 262) a third falling edge (e.g., the next falling edge 224) of the clock signal 56. In response to receiving the third falling edge 224, the I/O interface 16 (process block 264) the fourth gated data 220 (e.g., the fourth shaded portion 226 of the fourth gated data 220). In some embodiments, the fourth gated data 220 may additionally or alternatively be captured and output from the memory device 10 at a third rising edge 228 of the inverted clock signal 204.

As such, the method 240 may capture and output multiple sets of requested data 52, 202, 152, 218 in the data paths 46 from the memory device 10 based on rising and falling edges of an input clock signal 56, wherein the read delay 66 is approximately equal to the period 68 of the clock signal 56.

Figure 12:
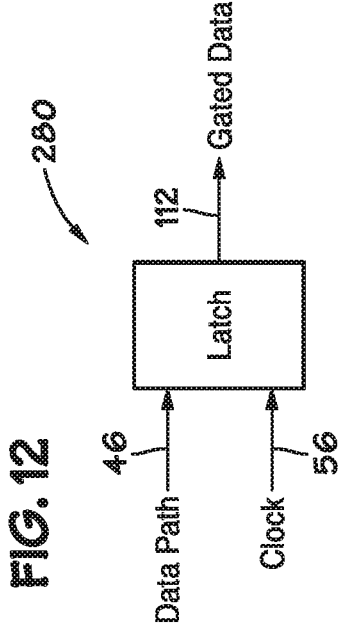
FIG. 12 is a schematic diagram of a latch that may gate a data path, according to an embodiment of the present disclosure.

FIG. 12 is a schematic diagram of a latch 280 that may gate the data path 46, according to an embodiment of the present disclosure. As illustrated, the latch 280 may receive as inputs the data path 46 and the clock signal 56 (e.g., via input pins). In some embodiments, the latch 280 may include additional inputs, such as the inverted clock signal 204, a disable data signal that may disable the latch 280 from passing data and/or storing data, and set and reset signals that may manipulate the gated data 112.

When the clock signal 56 is low, the latch 280 may enable the data path 46 to flow through the latch 280 and be output as the gated data 112. As such, in the example timing diagram 200 of FIG. 10, for example, after the first falling edge 114 of the clock signal 56 (and after a latch delay 116), the gated data 112 is the data 52.

When the clock signal 56 is high 62, the latch 280 may gate the data path 46 to be stored and output as the gated data 112 for the duration of clock signal 56 being high 62. As such, in the example timing diagram 200 of FIG. 10, for example, after the second rising edge 94 of the clock signal 56, the gated data 112 (e.g., the shaded portion 118 of the gated data 112) is the data 52 for the duration of clock signal 56 being high 62. In this manner, if other data or no data is present on the data path 46 after the data 52 is on the data path 46 while the clock signal 56 is high 62, reading and outputting the gated data 112 will continue to read and output the requested data 52.

Figure 13:
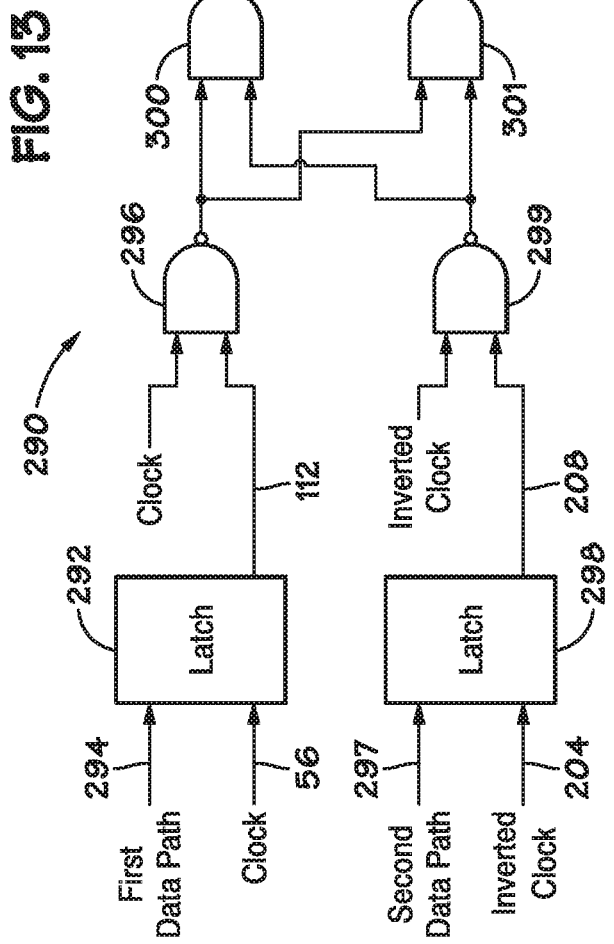
FIG. 13 is a diagram of a system that ensures that requested data in a data path is captured and output by the memory device 10 of FIG. 1, wherein a read delay is approximately equal to a period of an input clock signal, according to an embodiment of the present disclosure

FIG. 13 is a diagram of a system 290 that ensures that requested data in the data path 46 is captured and output by the memory device 10 of FIG. 1 when the read delay 66 is greater than half of (e.g., approximately equal to) the period 68 of the clock signal 56, according to an embodiment of the present disclosure. The system 290 may, for example, perform the methods 130, 170, and 240 of FIGS. 7, 9, and 11.

The system 290 may include a first latch 292, which may be similar to latch 280 as described in FIG. 12. The first latch 292 may include a first data path 294 (a data path of the data paths 46) and the clock signal 56 as inputs. Based on at least these inputs, the first latch 292 may output first gated data (e.g., gated data 112). The clock signal 56 and the first gated data 112 may also be input into a first NAND gate 296.

The system 290 may also include a second latch 298, which may be similar to the latch 280 as described in FIG. 12. The second latch 298 may include a second data path 297 (a data path of the data paths 46) and an inverted clock signal 204 as inputs. In some embodiments, the second latch 298 may instead receive the clock signal 56, and generate the inverted clock signal 204 (e.g., via an inverter). Based on at least these inputs, the second latch 298 may output second gated data (e.g., gated data 208). The inverted clock signal 204 and the second gated data 208 may also be input into a second NAND gate 299. The NAND gates 298, 299 gate the output of the latches 292, 298, respectively, to block data through the latches 292, 298 while the respective clock is low. The outputs of the first NAND gate 296 and the second NAND gate 299 may then be input into two subsequent NAND gates 300, 301. The subsequent NAND gates 300, 301 ensure that there is no data conflict on an output 302 between the outputs of the latches 292, 298. In other words, the system 290 may generate the output 302 based on the outputs of the two subsequent NAND gates 300, 301. In this manner, the requested data 52 may be properly output from the memory device 10.

Figure 14:
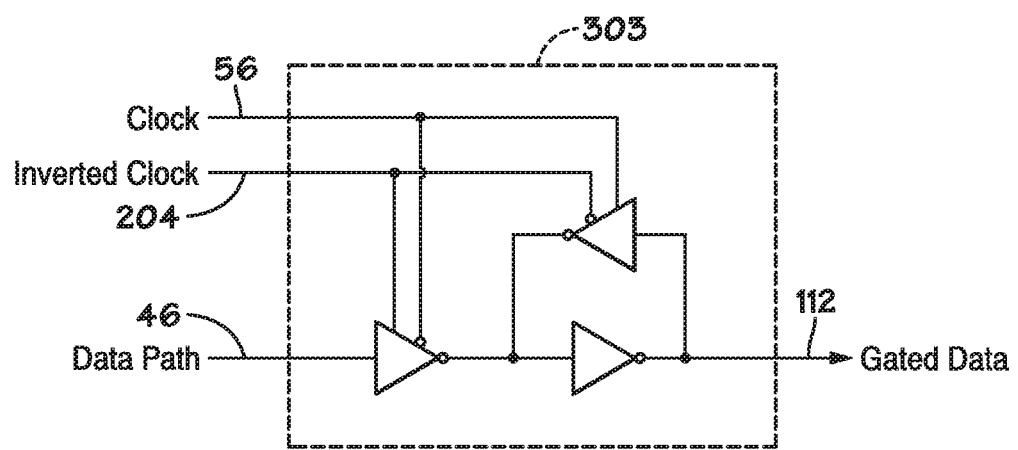
FIG. 14 is a schematic diagram of a latch that may gate a data path, according to an embodiment of the present disclosure.

FIG. 14 is a schematic diagram of a latch 303 that may gate the data path 46, according to an embodiment of the present disclosure. In some embodiments, the latch 303 may be used as the latch 280 of FIG. 12 and/or the latches 292, 298 of FIG. 13. As illustrated, the latch 303 may receive as inputs, via input pins, the clock signal 56, the inverted clock signal 204, and the data path 46. Based on at least these inputs and the circuitry (e.g., inverters) in the latch 303, the latch 303 may output the gated data 112.

Figure 15:
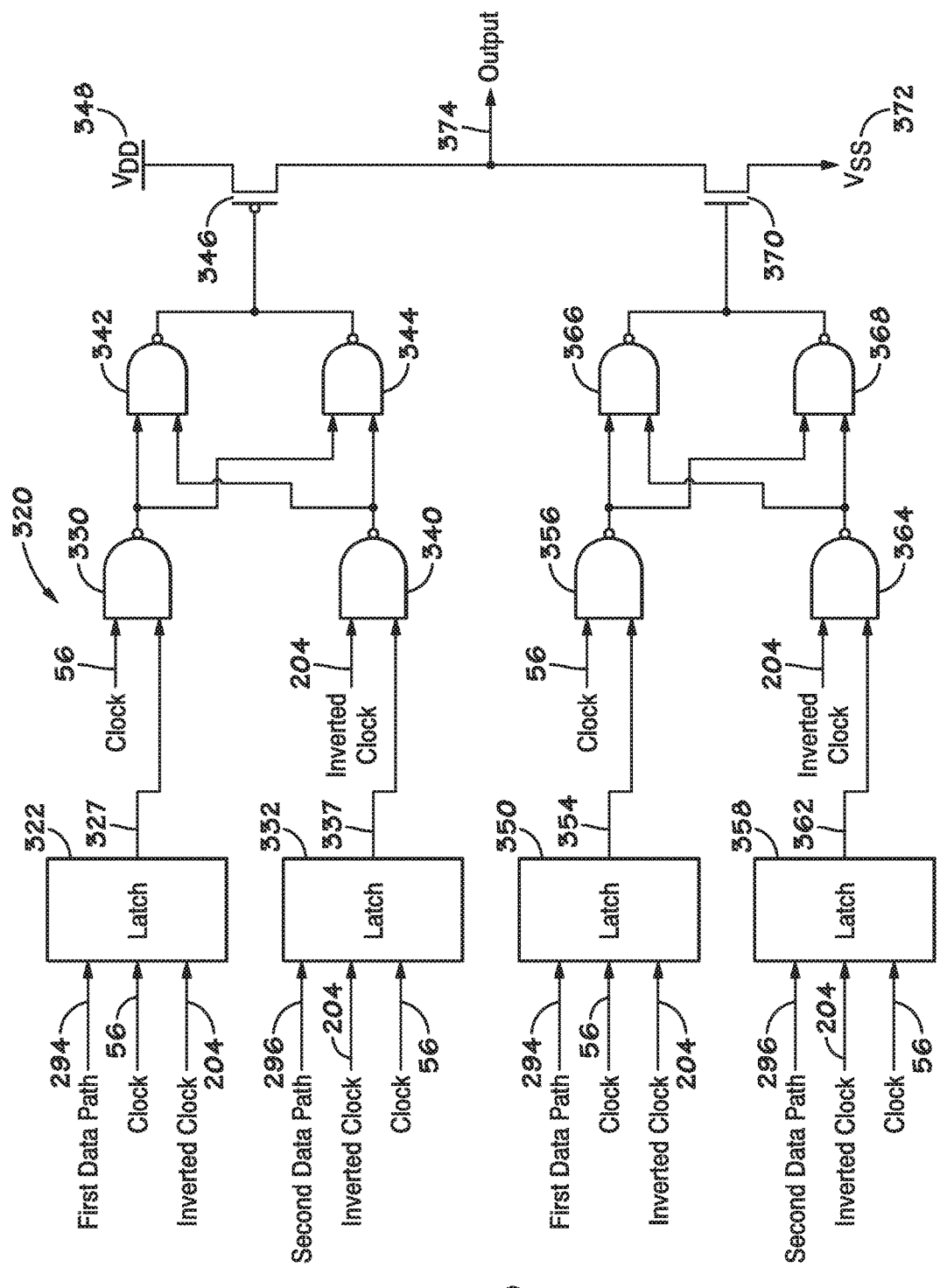
FIG. 15 is a diagram of a system that ensures that requested data in a data path is captured and output by the memory device 10 of FIG. 1, wherein a read delay is approximately equal to a period of an input clock signal, according to an embodiment of the present disclosure.

FIG. 15 is a diagram of a system 320 that ensures that requested data in the data path 46 is captured and output by the memory device 10 of FIG. 1, wherein the read delay 66 is approximately equal to the period 68 of the clock signal 56, according to an embodiment of the present disclosure. The system 320 may, for example, perform the methods 130, 170, and 240 of FIGS. 7, 9, and 11.

The system 320 may include a first latch 322, which may include a latch similar to latch 303 as described in FIG. 14. The first latch 322 may include as inputs: a first data path 294, the clock signal 56, and the inverted clock signal 204. Based on at least these inputs, the first latch 322 may output the first gated data 327. The clock signal 56 and the first gated data 327 may then be input into a first NAND gate 330.

The system 320 may also include a second latch 332, which may include a latch similar to the latch 303 as described in FIG. 14. The second latch 332 may include as inputs: a second data path 297, the inverted clock signal 204, and the clock signal 56. Based on at least these inputs, the second latch 332 may output second gated data 337. The inverted clock signal 204 and the second gated data 337 may then be input into a second NAND gate 340. The outputs of the first NAND gate 330 and the second NAND gate 340 may then be input into third and fourth NAND gates 342, 344. The outputs of the third and fourth NAND gates 342, 344 may be combined and input into a first switch 346, which may also include as an input a positive power supply VDD 348.

The system 320 may also include a third latch 350, which may include a latch similar to the latch 306 as described in FIG. 15. The third latch 350 may include as inputs: the first data path 294, the clock signal 56, and the inverted clock signal 204. Based on at least these inputs, the third latch 350 may output the third gated data 354. The clock signal 56 and the third gated data 354 may then be input into a fifth NAND gate 356.

The system 320 may also include a fourth latch 358, which may include a latch similar to the latch 306 as described in FIG. 15. The fourth latch 358 may include as inputs: the second data path 297, the inverted clock signal 204, and the clock signal 56. Based on at least these inputs, the fourth latch 358 may output the fourth gated data 362. The inverted clock signal 204 and the fourth gated data 362 may then be input into a sixth NAND gate 364. The outputs of the fifth NAND gate 356 and the sixth NAND gate 364 may then be input into seventh and eighth NAND gates 366, 368. The outputs of the seventh and eighth NAND gates 366, 368 may be combined and input into a second switch 370, which may also include as an input a negative power supply $V_{SS}$ 372. The outputs of the first switch 346 and the second switch 370 may be combined into output 374, which may be output from the memory device 10 (e.g., via one or more of the DQ signals 44). In this manner, the requested data 52 may be properly and freely output from the memory device 10. In some embodiments, the system 320 may include additional circuitry, such as buffer stages, between the NAND gates 342, 344 and the switch 346 and/or between the NAND gates 366, 368 and the switch 370.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is intended to cover all modifications, equivalents, and alternatives falling within the spirit and scope of the present disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. An apparatus comprising:
one or more memory banks configured to store data;
a data path coupled to the one or more memory banks and configured to transfer the data;
a latch configured to gate the data path based on a clock signal in the system; and
interface circuitry coupled to the data path, wherein the interface circuitry is configured to:
send an instruction to the one or more memory banks to transmit the data on the data path based on the clock signal; and
output gated data based on the clock signal, wherein the latch is configured to gate the data path to store the gated data based on the clock signal.

2. The apparatus of claim 1, wherein the interface circuitry is configured to send the instruction in response to receiving a first rising edge of the clock signal.

3. The apparatus of claim 1, wherein the interface circuitry is configured to output the gated data in response to receiving a second rising edge of the clock signal.

4. The apparatus of claim 1, wherein the latch is configured to gate the data path to store the gated data in response to receiving a falling edge of the clock signal.

5. The apparatus of claim 1, wherein the interface circuitry is configured to:
send a second instruction to the one or more memory banks to transmit second data on the data path based on an inverted clock signal; and
output gated data based on the inverted clock signal, wherein the latch is configured to gate the data path to store the gated data based on the inverted clock signal.

6. The apparatus of claim 5, wherein the interface circuitry is configured to send the second instruction in response to receiving a first rising edge of the inverted clock signal.

7. The apparatus of claim 5, wherein the interface circuitry is configured to output the gated data in response to a second rising edge of the inverted clock signal.

8. The apparatus of claim 5, wherein the latch is configured to gate the data path to store the gated data in response to a first falling edge of the inverted clock signal.

9. The apparatus of claim 5, wherein the inverted clock signal comprises an inversion of the clock signal.

10. An apparatus comprising:
one or more memory banks configured to store first data and second data;
a first data path coupled to the one or more memory banks configured to transfer the first data;
a second data path coupled to the one or more memory banks configured to transfer the second data;
a first latch configured to gate the first data path based on a clock signal in the semiconductor device;
a second latch configured to gate the second data path based on an inverted clock signal;
a first set of logic gates that receives and combines outputs of the first latch and the second latch and provides the combined outputs of the first latch and the second latch to a first transistor coupled to a positive power supply;
a third latch configured to gate the first data path based on the clock signal;
a fourth latch configured to gate the second data path based on the inverted clock signal;
a second set of logic gates that receives and combines outputs of the third latch and the fourth latch and provides the combined outputs of the third latch and the fourth latch to a second transistor coupled to a negative power supply; and
interface circuitry coupled to the one or more memory banks, the first latch, and the second latch, wherein the interface circuitry is configured to:
send a first instruction to the one or more memory banks to transmit the first data on the first data path;
send a second instruction to the one or more memory banks to transmit the second data on the second data path;
output first gated data based on the clock signal; and
output second gated data based on the inverted clock signal.

11. The apparatus of claim 10, wherein the first gated data is gated by the first latch.

12. The apparatus of claim 10, wherein the first gated data is gated by the third latch.

13. The apparatus of claim 10, wherein the second gated data is gated by the second latch.

14. The apparatus of claim 10, wherein the second gated data is gated by the fourth latch.

15. The apparatus of claim 10, wherein the interface circuitry is configured to send the first instruction in response to receiving a first rising edge of the clock signal.

16. The apparatus of claim 10, wherein the interface circuitry is configured to output first gated data in response to receiving a second rising edge of the clock signal.

17. The apparatus of claim 10, wherein the interface circuitry is configured to send the second instruction in response to receiving a first rising edge of the inverted clock signal.

18. The apparatus of claim 17, wherein the interface circuitry is configured to output second gated data in response to receiving a second rising edge of the inverted clock signal.

19. The apparatus of claim 10, wherein the first latch is configured to gate the first data path to store the first gated data in response to receiving a first falling edge of the clock signal, and wherein the second latch is configured to gate the second data path to store the second gated data in response to receiving a first falling edge of the inverted clock signal.

20. The apparatus of claim 10, wherein the third latch is configured to gate the first data path to store the first gated data in response to receiving a first falling edge of the clock signal, and wherein the fourth latch is configured to gate the second data path to store the second gated data in response to receiving a first falling edge of the inverted clock signal.

21. A tangible, non-transitory, machine-readable-medium, comprising machine-readable instructions that, when executed by a processor, cause the processor to:
receive a first rising edge of a clock signal;
send a first instruction to transmit data on a first data path in response to receiving the first rising edge of the clock signal;
receive a falling edge of the clock signal;
gate the first data path to store first gated data in response to receiving the falling edge of the clock signal;
receive a second rising edge of the clock signal; and
output the first gated data in response to receiving the second rising edge of the clock signal.

22. The tangible, non-transitory, machine-readable-medium of claim 21, comprising machine-readable instructions that, when executed by the processor, cause the processor to:
receive a first rising edge of an inverted clock signal;
send a second instruction to transmit data on a second data path in response to receiving the first rising edge of the inverted clock signal;
receive a falling edge of the inverted clock signal;
gate the second data path to store second gated data in response to receiving the falling edge of the inverted clock signal;
receive a second rising edge of the inverted clock signal; and
output the second gated data in response to receiving the second rising edge of the inverted clock signal.

* * * * *